(12) United States Patent
Castaneda et al.

(10) Patent No.: US 8,551,153 B2
(45) Date of Patent: Oct. 8, 2013

(54) PROSTHESIS COMPRISING A COILED STENT AND METHOD OF USE THEREOF

(75) Inventors: Alfredo Castaneda, Miami, FL (US); Donald Francis DePalma, Weston, FL (US); Clifford J. Dwyer, Weston, FL (US); Kirk L. Johnson, Davie, FL (US)

(73) Assignee: Cordis Corporation

( * ) Notice: Subject to any disclaimer, the term of this patent is extended or adjusted under 35 U.S.C. 154(b) by 968 days.

(21) Appl. No.: 11/312,073

(22) Filed: Dec. 20, 2005

(65) Prior Publication Data
US 2007/0142895 A1  Jun. 21, 2007

(51) Int. Cl.
*A61F 2/06* (2013.01)

(52) U.S. Cl.
USPC ..................................... 623/1.13

(58) Field of Classification Search
USPC ........... 623/1.13, 1.15, 1.16, 1.35, 1.44, 1.31, 623/1.33
See application file for complete search history.

(56) References Cited

U.S. PATENT DOCUMENTS

| | | | | |
|---|---|---|---|---|
| 4,160,448 A | * | 7/1979 | Jackson | 600/486 |
| 5,383,928 A | * | 1/1995 | Scott et al. | 623/1.12 |
| 5,576,517 A | * | 11/1996 | Wojnarowski et al. | 174/262 |
| 5,836,966 A | | 11/1998 | Germain | |
| 6,656,218 B1 | | 12/2003 | Denardo et al. | |
| 6,752,826 B2 | * | 6/2004 | Holloway et al. | 623/1.13 |
| 7,112,217 B1 | * | 9/2006 | Kugler et al. | 623/1.31 |
| 2001/0003801 A1 | * | 6/2001 | Strecker | 623/1.11 |
| 2001/0020173 A1 | * | 9/2001 | Klumb et al. | 606/194 |
| 2002/0173840 A1 | * | 11/2002 | Brucker et al. | 623/1.16 |
| 2003/0040803 A1 | | 2/2003 | Rioux | |
| 2003/0130720 A1 | * | 7/2003 | DePalma et al. | 623/1.13 |
| 2004/0034406 A1 | * | 2/2004 | Thramann | 623/1.13 |
| 2004/0117003 A1 | * | 6/2004 | Ouriel et al. | 623/1.35 |
| 2005/0080481 A1 | * | 4/2005 | Madda et al. | 623/1.22 |
| 2005/0203499 A1 | * | 9/2005 | Pendekanti et al. | 606/27 |
| 2006/0095116 A1 | * | 5/2006 | Bolduc et al. | 623/1.16 |
| 2007/0185562 A1 | * | 8/2007 | Furst | 623/1.15 |
| 2008/0132996 A1 | * | 6/2008 | Drasler et al. | 623/1.15 |

FOREIGN PATENT DOCUMENTS

| | | |
|---|---|---|
| JP | 2001087394 A | 4/2001 |
| JP | 2004509662 A | 4/2004 |
| JP | 2005058459 A | 3/2005 |
| WO | WO 95/18585 A1 | 7/1995 |
| WO | WO 99/47071 A1 | 9/1999 |
| WO | WO 00/49973 A2 | 8/2000 |

OTHER PUBLICATIONS

Klempner, D. & Sendijarevic, V. (2004). Handbook of Polymeric Foams and Foam Technology ($2^{nd}$ ed.). Munich, Germany: Hanser.*
Japanese Notification of Reasons for Refusal mailed on Oct. 25, 2011 from corresponding Japanese Patent Application No. 2006-341267.
European Search Report dated Aug. 18, 2008 for corresponding European Patent Application No. 06256410.9-1526.

* cited by examiner

Primary Examiner — Thomas McEvoy

(57) ABSTRACT

The present invention is directed to a prosthesis and method for treating, repairing, and/or replacing an abdominal aortic aneurysm. The prosthesis includes a coiled stent comprised of shape memory material having first and second anchoring zones and an intermediate zone. The prosthesis also includes graft material engaging at least a portion of the stent. During delivery of the prosthesis, the stent is in a substantially straight longitudinal configuration, and after delivery of the prosthesis the stent is returned to a coiled configuration. The diameter of the prosthesis may be adjusted by controlling the degree to which the stent is coiled.

6 Claims, 1 Drawing Sheet

PROSTHESIS COMPRISING A COILED STENT AND METHOD OF USE THEREOF

BACKGROUND OF THE INVENTION

1. Field of the Invention

The present invention relates to devices and methods for repairing abdominal aortic aneurysms. More particularly, the present invention relates to a prosthesis comprising a coiled stent.

2. Discussion of the Related Art

An endoprosthesis or stent-graft is commonly used as a tubular structure left inside the lumen of a duct to relieve an obstruction. Commonly, endoprostheses are inserted into the lumen in a non-expanded form and are then expanded autonomously or with the aid of a second device in situ. The endoprosthesis may be self expanding or expansion may occur through the use of a catheter mounted angioplasty balloon in order to shear and disrupt the obstructions associated with the wall components of the vessel and to obtain an enlarged lumen. In the absence of an endoprosthesis, restenosis may occur as a result of elastic recoil of the stenotic lesion.

While the percutaneous placement of endoprostheses represent a significant improvement over conventional surgical techniques, there is a need to improve the endoprostheses, their method of use, and their applicability to varied biological conditions. Further, there is a need to reduce or eliminate repeat medical procedures, and a need for increasing the number of patients that are candidates for procedures involving endoprostheses.

The most common difficulties may be derived from attempts to produce endoprostheses with minimal profile, that minimizes graft wear, and that resists fatigue failure. Further, such devices should be simple to position and reposition as necessary, provide a fluid tight seal, and be deployable into a varied number of shapes and diameters as dictated by the physiological condition of the patient.

SUMMARY OF THE INVENTION

In accordance with the present invention, a means is provided for overcoming the problems associated with the prior art as briefly described above.

An aspect of the present invention is directed to a prosthesis including a stent comprised of shape memory material and graft material engaging at least a portion of the stent. The stent may be in a substantially straight configuration during delivery of the prosthesis within an interior wall of a lumen, and after delivery of the prosthesis the stent may be returned to a coiled configuration.

More particularly, the stent is attached to the interior surface or the exterior surface of the graft material. In addition, the shape memory material may be comprised of Nickel Titanium alloys (Nitinol). Furthermore, the stent may be returned to a coiled configuration by feeding an additional length of the stent within the lumen.

The present invention is also related to a method for repairing an abdominal aortic aneurysm comprising delivering at least one prosthesis within the interior wall of a lumen. The prosthesis includes a stent comprised of shape memory material and graft material engaging at least a portion of the stent. During delivery of the prosthesis, the stent is in a substantially straight configuration, and after delivery of the prosthesis the stent is returned to a coiled configuration.

More particularly, the stent may be returned to a coiled configuration by feeding an additional length of the stent within the lumen. During delivery of the prosthesis, the graft material preferably has a profile diameter less than about fourteen French (14 F), which is approximately 4.7 millimeters, more preferably the graft material has a profile diameter less than about nine (9) F which is approximately 3.0 millimeters. The proximal end and/or the distal end of the prosthesis is anchored within the interior wall of the lumen via a first and second anchoring zone, respectively. For example, the proximal and/or distal end of the prosthesis may be anchored by returning the stent to a coiled configuration or by attaching the prosthesis to another stent located within the interior wall of the lumen.

BRIEF DESCRIPTION OF THE DRAWINGS

The foregoing and other aspects of the present invention will best be appreciated with reference to the detailed description of the invention in conjunction with the accompanying drawings wherein.

DETAILED DESCRIPTION OF THE PREFERRED EMBODIMENTS

Definitions

Figure 1:
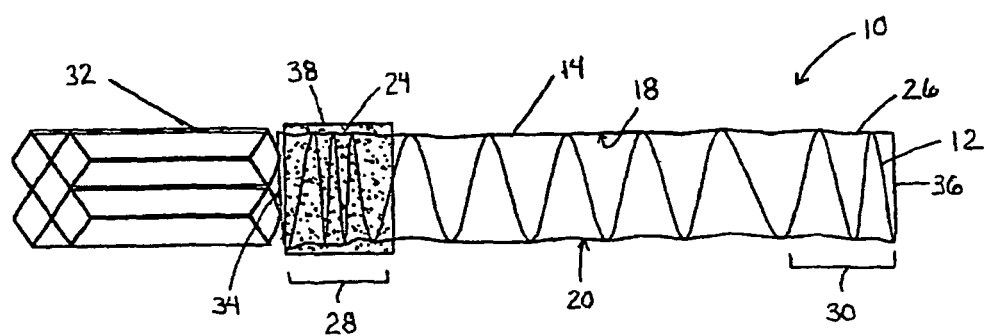
FIG. 1 is a side view of a prosthesis of the present invention attached to a transrenal stent.

As used herein, aortic aneurysm refers to any failure of a conduit, such as an aortic wall, typically characterized by an undesirable dilation of a portion of the artery, vessel malformation, or an occlusion. The methods and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. An exemplary use of a methods and structures of the present invention is to repair an aortic aneurysm, and the use of such term is not intended to limit the use of the methods or structures of the present invention to repair or replace other conduit failures. The structures and methods of the present invention may also be utilized in the thoracic aorta, and may be used to repair thoracic aneurysms or thoracic dissecting aneurysms. Accordingly, use of the term "aortic aneurysm" is intended to relate to and include other aneurysms, including but not limited to both abdominal aortic aneurysms and thoracic aneurysms.

In preferred embodiments of the invention, the methods and structures are used to treat, repair, replace, or bypass an abdominal aortic aneurysm. As used herein fluid pathway refers to any in vivo structure through which a biological fluid passes. A preferred fluid pathway is an artery. Fluid pathways include, but are not limited to channels formed by an artery" a vein, a capillary, lymph nodes and channels, and arteries, veins, and capillaries within an organ or organelle.

As used herein fluid or biological fluid refers to any fluid produced by an animal, including a human. Exemplary biological fluids include, but are not limited to blood, oxygenated blood, de-oxygenated blood, gastric fluids, amniotic fluid, spinal fluid, and lymph. The preferred fluid is blood or oxygenated blood.

As used herein, adapted for communication, communicating, or similar terms refer to any means, structures, or methods for establishing operational association between two elements of the system. Similarly, engaging, adapted to engage, or similar terms refer to means, structures, or methods for contacting a first component, structure, or portion thereof with a second component, structure, or portion thereof. Exemplary structures are shown in the Figures. Typically, all of these terms and phrases refer to at least one structure in or on a first component configured to engage a complementary structure in or on a second component, and the use of these inter-engaging features to link a first component with a second component. The engagement or communication may be matingly (e.g., permanent) and/or releasably (e.g., temporary) linked. In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another graft or prosthesis. As used herein, connector refers to any structure used to form a joint or to join itself to another component or portion thereof. These connectors or connections establish a fluid flow path through various elements of the apparatus, assembly, or system. In a preferred embodiment of the invention, the methods or structures are intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, e.g., referring to a position farthest from the beginning; in human anatomy, it is important to note the distinction between the term distal and the terms caudal or inferior which commonly refer to a lower portion or a portion located below. Distal as used with catheter delivery systems refers to a location or position farthest from the position on the catheter which is located outside the body. Proximal is used in accordance with its ordinary dictionary definition, e.g., referring to a position nearest the beginning; in human anatomy, it is important to note the distinction between the term proximal and the terms cranial or superior which commonly refer to a upper portion or a portion located above. Proximal as used with catheter delivery systems refers to a location or position closest from the position on the catheter which is located outside the body. The terms distal and proximal are also intended to convey opposite ends or portions of a device, channel, element, or structure.

In relation to a fluid flow path, distal will typically refer to a downstream location in the fluid flow path, and proximal will typically refer to an upstream location, unless otherwise specifically noted. Anatomically, distal generally refers to "away from the heart" and proximal generally refers to "toward the heart." Thus in the case of treatment of abdominal aortic aneurysms, proximal refers to the superior or upstream position while distal refers to the inferior or downstream position which in most cases is a position located in the lilacs.

The apparatuses and methods of the present invention may be used in the treatment of aortic aneurysms, preferably an abdominal aortic aneurysm, among other uses noted below. A better understanding of the present device and its use in treating aortic aneurysms will be achieved by reading the following description in conjunction with the following incorporated references.

Figure 2:
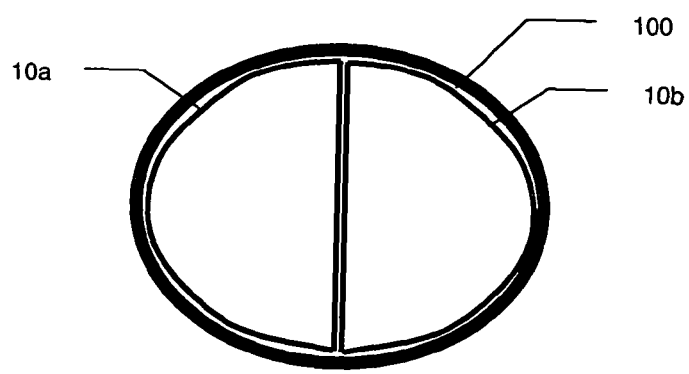
FIG. 2 is a cross-sectional view showing the proximal ends of two of the prostheses of the present invention located within a vessel

Referring to FIG. 1, shown is a prosthesis 10 including a stent 12 and graft material 14 engaging at least a portion of the stent. In treating abdominal aortic aneurysms, at least one of the prosthesis 10 in accordance with the present invention is utilized. Preferably two of the prostheses 10a and 10b are utilized and delivered in a parallel fashion such that the proximal or superior ends form a cross-section within the lumen of the vessel 100. This is sometimes referred to as a double D configuration, as shown in FIG. 2. The distal or inferior ends would be located in each of the respective iliac arteries or either one may be attached to additional stent grafts when additional length is required.

The stent 12 is comprised of shape memory material which has been shape set in a spiral or coiled configuration. In a preferred embodiment the stent is a one piece smooth, single spiral coil formed from elongate, straight, single member as illustrated in FIG. 1. The shape memory material may be comprised of various materials including but not limited to metal and metal alloys. Preferably, the shape memory material is comprised of nitinol. The stent 12 maintains lumen patency in the prosthesis 10 while maintaining flexibility. In preferred embodiments, of the present invention, the stent 12 defines a channel through which a fluid, such as blood, may flow.

The graft material 14 may be made from any number of materials known to those having skill in the art, including but not limited to woven polyester, Dacron®, Teflon®, Vectran®, polyurethane, porous polyurethane, silicone, polyethylene terephthlate, expaned polytetrafluoroethylene (ePTFE) and blends of various materials.

In some embodiments of the present invention, it may be desirable to incorporate a biodegradable, or degradable material, such as albumin, or a collagen. A graft material 14 that is biodegradable would erode or dissolve over time; however it is believed that a layer of endothelium may grow as the graft material erodes. It is further believed that these new layers of endothelium may provide a new, fluid impervious lining within the aneurysm.

It is preferred that all of the foregoing materials be porous to allow for an intimal layer to form a biofusion structure or matrix.

The graft material 14 may be variously configured, preferably to achieve predetermined mechanical properties. For example, the graft material 14 may incorporate a single or multiple weaving and/or pleating patterns, or may be pleated or unpleated. For example, the graft 14 may be configured into a plain weave, a satin weave, include longitudinal pleats, interrupted pleats, annular or helical pleats, radially oriented pleats, or combinations thereof. Alternatively, the graft material 14 may be knitted or braided. In the embodiments of the present invention in which the graft material 14 is pleated, the pleats may be continuous or discontinuous. Also, the pleats may be oriented longitudinally, circumferentially, helically, or combinations thereof.

In accordance with the present invention, the graft material 14 may be impervious or substantially impervious to the flow of blood, or may be porous or permeable.

A graft material 14 is impervious if it prevents blood from passing through the graft material on contact with blood or after the graft material is saturated with blood. Choice of the flow characteristics of a graft material 14 are well known to those skilled in the art, and are tied in part to the intended function of the prosthesis 10 or portion of the prosthesis.

The foregoing graft material 14 may be knitted or woven, and may be warp or weft knitted. If the graft material 14 is warp knitted, it may be provided with a velour, or towel like surface; which is believed to speed the formation of blood clots, thereby promoting the integration of a prosthesis 10 or prosthesis component into the surrounding tissue or cellular structure.

In accordance with the present invention, it may be highly desirable to provide a graft material 14 that limits or eliminates the amount of blood that passes between the graft material and the arterial wall, to provide a catheter-delivered graft or prosthesis 10 that extends through a longer portion of an artery, to improve the anchoring mechanisms between two prostheses, to improve the anchoring mechanism between the prosthesis 10 and the arterial wall or an intraluminal cavity within an artery, and to improve the fluid dynamic and performance characteristics of the implanted prosthesis.

The stent 12 may be attached to the graft material 14 by any number of attachment means or methods known to those skilled in the art, including friction (if placed inside the graft); adhesives, such as polyurethane glue; a plurality of conventional sutures of polyvinylidene fluoride, polypropylene, Dacron®, or any other suitable material; ultrasonic welding; mechanical interference fit; loops; folds; sutures; and staples. The stent 12 may be attached to the interior surface 18 or exterior surface 20 of the graft material 14 by any of the attachment means or methods described above. Preferably, the stent 12 is pre-threaded through the attachment means such as loops, folds or sutures located on the graft material 14. An external attachment of the stent 12 to the graft material 14 is preferred because it minimizes graft to stent motion, and thereby prevents wear of the graft material.

Prior to and during delivery of the prosthesis 10 within the interior wall of a lumen, the graft material 14 is crimped (or unexpanded) and has a low profile diameter. Preferably, the graft material 14 has a low profile diameter less than about fourteen (14) French, which is approximately 4.7 mm.

Prior to delivery of the prosthesis 10, the shape memory stent 12 is pulled into a substantially straight longitudinal configuration. The straight configuration of the stent 12, in addition to the low profile of the graft material 14 greatly reduces the overall profile of the delivery system needed to deliver the prosthesis 10 within the lumen. Thus, the longitudinal pre-delivered configuration of the stent 12 together with the low profile of the graft material 14 when combined to form prosthesis 10 of the present invention enables the delivery system to be significantly smaller, and accordingly it may be used in a greater variety of applications, including but not limited to abdominal aneurysms with highly tortuous iliac arteries or small iliac arteries typically found in smaller individuals as well as women as well as in branch vessels coming off the larger diameter main vessel. After the prosthesis 10 is delivered within the lumen, the stent 12 is returned to its shape memory coiled configuration which expands the graft material 14 and provides support to the graft material 14, and thus provides support, radial strength and improved flexibility to the entire length of the prosthesis 10. Specifically, the stent 12 supports the inside diameter of the graft material 14 and the prosthesis 10. The stent 12 may be returned to a coiled configuration by feeding an additional length of the stent within the lumen. The diameter of the prosthesis 10 may be adjusted, e.g. to fit the size of the lumen, by controlling the degree to which the stent 12 is coiled. For example, the more coiled the stent 12 is, the greater the diameter of the prosthesis 10 will be. Conversely, the less coiled the stent 12 is, the smaller the diameter of the prosthesis 10 will be. This may be accomplished by feeding more or less of an additional length of stent 12 within the lumen.

The coiled design of the stent 12 is resistant to fatigue failure and wear of the prosthesis 10 because it is able to distribute forces more evenly throughout the length of the coil, and accordingly, the prosthesis. In addition, the coil configuration eliminates sharp ends that focus or concentrates forces and motion on a specific graft area 14, and thereby prevents and/or decreases graft material wear zones.

The stent 12 of the present invention may be coated with a variety of materials and/or drugs, for example, to reduce friction between the stent and the graft material 14, to reduce thrombus, and/or to promote cell growth for better healing responses in patients. Such materials and drugs include but are not limited to heparin and growth factor.

During or after delivery of the prosthesis 10 into the lumen, the proximal or superior end 24 and/or the distal or inferior end 26 of the prosthesis are anchored within the interior wall of the lumen. The prosthesis 10 preferably includes a first anchoring zone 28 and a second anchoring zone 30 and an intermediate zone disposed there between. The first and second anchoring zones 28 and 30 may be used to anchor the proximal or superior end 24 and the distal or inferior end 26, respectively. The first and second anchoring zones 28 and 30 may anchor the prosthesis 10, including the proximal end 24 and/or the distal end 26, respectively, by any means known to those having skill in the art, including but not limited to, attaching each anchoring zone 28 and 30 to another stent or prosthesis, such as a separate cut and expanded stent or prosthesis. The secondary stent or prosthesis which is attached to the first or second anchoring zone 28 and 30 may be located within the interior wall of the lumen prior to delivery of the prosthesis 10 within the lumen. For example, the first anchoring zone 28 of the prosthesis 10 may be attached to a trans-renal stent 32 located within the lumen, as illustrated in FIG. 1. In addition, the second anchoring zone 30 of the prosthesis 10 may be attached to a super-renal stent located within the lumen, thereby providing anchoring above the renal arteries with the prosthesis 10 deployed below the renal arteries.

Furthermore, the first anchoring zone 28 and/or the second anchoring zone 30 of the prosthesis 10 may be anchored within the interior wall of the lumen as the stent 12 is returned to a coiled configuration post delivery, thereby causing the respective end(s) of the prosthesis to be supported against the interior wall of the lumen. This may be achieved by decreasing the ring to ring distance of the coil within the anchoring zones 28 and 30 as illustrated in FIG. 1. Although the ring to ring distance can vary, the preferred ring to ring distance of the anchoring zones is two (2) to five (5) millimeters, while the preferred ring to ring distance of the intermediate zone is four (4) to ten (10) millimeters. One skilled in the art will readily recognize that changing the number of coils in a defined area of the stent 12 alters the stiffness, flexibility, and/or outward force. In accordance with the present invention, it may be desirable to provide an anchoring segment 28 and 30 with an increased number of coils to impart greater stiffness and outward force to that area of the prosthesis 10 or system. If desired, the coil of stent 12 may be configured into segments (not limited to the anchoring zones 28 and 30) having different or varying frequencies or number of coils.

Alternatively, each anchoring zone 28 and 30 may be comprised of a non-grafted portion of the coiled stent 12 used as a bare stent to anchor the proximal end 24 and/or the distal end 26, respectively, of the prosthesis 10 within the lumen. This may be achieved by feeding the stent 12 beyond the proximal edge 34 of the graft material 14 to anchor the proximal end 24 of the prosthesis 10. Similarly, the distal end 26 of the prosthesis 10 may be anchored by feeding the stent 12 into the graft 14 so that an additional length of stent extends beyond the distal edge 36 of the graft material. In an alternative embodiment, the bare stent portion which extends beyond the first anchoring zone 28 and/or extends beyond the second anchoring zone 30 may be a conventional hypotube cut stent, or other balloon or self expanding stent with the coiled stent 12 located in the mid section of the prosthesis. The bare stent 12 segment of the first and second anchoring zones 28 and 30 may assist in long term stability of the prosthesis 10 as the bare stent segment becomes encapsulated with cell growth and eventually becomes embedded in the vessel wall.

In accordance with the present invention, in embodiments where the first anchoring zone 28 and/or the second anchoring zone 30 of the prosthesis 10 is anchored within the lumen via attachment to another stent or prosthesis as described above, a sealing device 38 may be delivered to the respective attachment site(s) to fill in any irregular openings between the first anchoring zone 28 or second anchoring zone 30 of the prosthesis 10 and the secondary stent or prosthesis. The sealing device 38 may be any sealing device known to those having skill in the art, including but not limited to foam, such as a foam plug or glues. Preferably, the sealing device 38 is a compressible foam which is expandable upon delivery and deployment of the sealing device.

In a another alternative embodiment, the graft material 14 may be delivered and deployed within the interior wall of a lumen first, and then the coiled stent 12 may be delivered within the graft using any of the methods and systems described herein.

A stent 12, graft material 14, and/or prosthesis 10 of the present invention may include one or more markers, including but not limited to radiopaque markers. In preferred embodiments of the invention, the markers are used to identify the position of the stent 12, graft material 14, or prosthesis 10 in relation to a body part and/or in relation to another prosthesis, and/or to identify the position of one part of the prosthesis relative to another part. In most preferred embodiments of the invention, the marker(s) is/are used to identify a position in vivo.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A prosthesis comprising:
   a single smooth, spiral coiled stent having a plurality of rings formed from an elongate, straight, single member of shape memory material, the stent including first and second anchoring zones and an intermediate zone, the first and second anchoring zones having a ring to ring distance in the range from about 2 mm to about 5 mm and the intermediate zone having a ring to ring distance in the range from about 4 mm to about 10 mm, and wherein the intermediate zone is longer than the first and second anchoring zones, at least one of the first and second anchoring zones being configured for mating with an additional prosthesis;
   a sealing device configured to fit over substantially all of the at least one of the first and second anchoring zones, the sealing device comprising a compressible foam; and
   graft material engaging at least a portion of the stent, the single member configured to be pulled into a substantially straight longitudinal configuration prior to delivery, and returned to the coiled configuration to expand the graft material.

2. The prosthesis of claim 1, wherein the shape memory material is comprised of a metal alloy.

3. The prosthesis of claim 1, wherein the stent is attached to an interior surface or an exterior surface of the graft material.

4. The prosthesis of claim 1, wherein during delivery of the prosthesis, the graft material has a profile diameter less than about fourteen French.

5. The prosthesis of claim 1 wherein the stent is coated with heparin.

6. The prosthesis of claim 1 further comprising a secondary stent attached to the first anchoring zone.

\* \* \* \* \*